(12) United States Patent
Bannantine

(10) Patent No.: US 9,145,456 B1
(45) Date of Patent: Sep. 29, 2015

(54) **HYBRIDOMAS PRODUCING HIGHLY SPECIFIC MONOCLONAL ANTIBODIES TO DETECT *MYCOBACTERIUM AVIUM* SUBSPECIES *PARATUBERCULOSIS***

(71) Applicant: The United States of America, as represented by the Secretary of Agriculture, Washington, DC (US)

(72) Inventor: John P. Bannantine, Ames, IA (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 0 days.

(21) Appl. No.: 14/036,102

(22) Filed: Sep. 25, 2013

Related U.S. Application Data (62) Division of application No. 12/951,434, filed on Nov. 22, 2010, now Pat. No. 8,658,386, and a division of application No. 12/319,911, filed on Dec. 17, 2008, now Pat. No. 7,851,170.

(60) Provisional application No. 61/009,291, filed on Dec. 27, 2007.

(51) Int. Cl.
  *C07K 16/12* (2006.01)
  *G01N 33/53* (2006.01)
  *G01N 33/536* (2006.01)

(52) U.S. Cl.
  CPC .............. *C07K 16/1289* (2013.01); *C07K 16/12* (2013.01); *G01N 33/53* (2013.01); *G01N 33/536* (2013.01)

(58) Field of Classification Search
  CPC . A61K 2039/51; A61K 39/00; C07K 16/1289
  USPC ........................ 424/150.1, 274.1; 530/388.4
  See application file for complete search history.

(56) References Cited

PUBLICATIONS

Fundamental Immunology, William E. Paul, M.D. ed., 3d ed., p. 242, 1993.*

* cited by examiner

*Primary Examiner* — Padma V Baskar
(74) *Attorney, Agent, or Firm* — John D. Fado; Howard V. Owens, Jr.

(57) ABSTRACT

Hybridoma cell lines which produce and secrete monoclonal antibodies which selectively bind to *Mycobacterium avium* subspecies *paratuberculosis* have been produced. Cells of *M. avium* subspecies *paratuberculosis* in biological samples may be detected and quantified by contacting the sample with the antibodies to form a *M. avium* subspecies *paratuberculosis*/antibody immunocomplex when *M. avium* subspecies *paratuberculosis* is present, which immunocomplex may then be detected. The monoclonal antibodies also may be incorporated into kits for the detection and quantification of *M. avium* subspecies *paratuberculosis*.

5 Claims, 1 Drawing Sheet

HYBRIDOMAS PRODUCING HIGHLY SPECIFIC MONOCLONAL ANTIBODIES TO DETECT *MYCOBACTERIUM AVIUM* SUBSPECIES *PARATUBERCULOSIS*

This is a divisional of Ser. No. 12/951,434, filed on Nov. 22, 2010, now issued as U.S. Pat. No. 8,658,386, which was a divisional of Ser. No. 12/319,911, filed on Dec. 17, 2008, now issued as U.S. Pat. No. 7,851,170 which claims the benefit under 35 U.S.C. 1.19(e) of U.S. provisional No. 61/009,291, filed Dec. 27, 2007, the contents of which are hereby incorporated by reference herein in their entirety.

BACKGROUND OF THE INVENTION

1. Field of the Invention

The invention relates to hybridoma cell lines and monoclonal antibodies produced therefrom which may be used to detect the bacterium *Mycobacterium avium* subspecies *paratuberculosis*.

2. Description of the Prior Art

The genus *Mycobacterium* comprises a diverse group of animal and human pathogens as well as saprophytes, many of which are ubiquitous in the environment. *Mycobacterium avium* subsp. *paratuberculosis* is a member of the *Mycobacterium avium* complex (MAC) and an animal pathogen that is highlighted by the large financial burden that it places on the dairy industry due to Johne's disease (JD). Figures extrapolated from the 1996 NAHMS dairy survey suggest that the cost of this disease was over $200 million per year (Ott et al. 1999. Herd-level economic losses associated with Johne's disease on US dairy operations. Prev. Vet. Med. 40:179-192). The growing recognition of *M. avium* subsp. *paratuberculosis* infection in wildlife species is of considerable concern, since it may affect our ability to control or eradicate JD from domesticated animals (Corn et al. 2005. Isolation of *Mycobacterium avium* subsp. *paratuberculosis* from free-ranging birds and mammals on livestock premises. Appl. Environ. Microbiol. 71:6963-6967; Daniels et al. 2003. The risk of disease transmission to livestock posed by contamination of farm stored feed by wildlife excreta. Epidemiol. Infect. 130:561-568).

Despite the research difficulties and economic consequences of JD, very few reports have described specific, antigen-based detection reagents for *M. avium* subsp. *paratuberculosis*. With the exception of a single study published 10 years ago (Mutharia et al. 1997. Analysis of culture filtrate and cell wall-associated antigens of *Mycobacterium paratuberculosis* with monoclonal antibodies. Infect. Immun. 65:387-394), the scientific literature is silent on the subject of *M. avium* subsp. *paratuberculosis* monoclonal antibodies (MAbs) and their use in JD research. Very recently, single-chain antibodies were selected by cloning heavy and light chains from sheep with JD (Berger et al. 2006. Isolation of high-affinity single-chain antibodies against *Mycobacterium avium* subsp. *paratuberculosis* surface proteins from sheep with Johne's disease. Clin. Vaccine Immunol. 13:1022-1029). This effort has resulted in two very promising recombinant antibodies; however, the *M. avium* subsp. *paratuberculosis* proteins that these antibodies react with remain unknown. The overall lack of detection reagents for *M. avium* subsp. *paratuberculosis* is in stark contrast to the availability of detection reagents for other bacterial pathogens of cattle, such as *Brucella* or *Mycobacterium bovis*, for which scores of MAbs are available to researchers (Bowden et al. 1997. Rapid identification of rough *Brucella* isolates by a latex coagglutination assay with the 25-kilodalton outer membrane protein and rough-lipopolysaccharide-specific monoclonal antibodies. Clin. Diagn. Lab. Immunol. 4:611-614; Cloeckaert et al. 1996. Production and characterization of monoclonal antibodies to *Brucella melitensis* cytosoluble proteins that are able to differentiate antibody responses of infected sheep from Rev. 1 vaccinated sheep. J. Med. Microbiol. 45:206-213; Kuchinka et al. 1990. Production and partial characterization of monoclonal antibodies to the neotype strain of *Mycobacterium bovis*. Am. J. Vet. Res. 51:1608-1615; Mertens et al. 2001. Selection of phage-displayed peptides recognized by monoclonal antibodies directed against the lipopolysaccharide of *Brucella*. Int. Rev. Immunol. 20:181-199; Morris et al. 1985. The identification of antigenic determinants on *Mycobacterium bovis* using monoclonal antibodies. J. Gen. Microbiol. 131:1825-1831; and Weynants et al. 1997. Characterization of smooth lipopolysaccharides and O polysaccharides of *Brucella* species by competition binding assays with monoclonal antibodies. Infect. Immun. 65:1939-1943).

Against this background, recent changes have modified the JD research landscape. Within the United States, a national consortium, entitled the Johne's Disease Integrated Program (JDIP), has identified the high research priorities and the knowledge gaps necessary to combat JD. Similar JD research consortiums have also recently formed in Europe and New Zealand. One of the priorities identified by JDIP is the development of specific detection reagents such as MAbs for *M. avium* subsp. *paratuberculosis*. More than just their obvious application for the diagnosis of JD, MAbs are critical reagents in cell biology and pathogenesis studies, including studies of macrophage-pathogen interactions, studies that use Luminex and magnetic bead technologies, as well as histopathology studies. MAbs that detect specific *M. avium* subsp. *paratuberculosis* proteins are ideal for incorporation into diagnostic assays such as those already developed for *Campylobacter* (Brooks et al. 2004. Evaluation of a monoclonal antibody-based enzyme-linked immunosorbent assay for detection of *Campylobacter fetus* in bovine preputial washing and vaginal mucus samples. Vet. Microbiol. 103:77-84) and *Escherichia coli* (Kerr et al. 2001. Development of a monoclonal sandwich ELISA for the detection of animal and human *Escherichia coli* O157 strains. J. Appl. Microbiol. 90:543-549). Furthermore, MAbs have application in the histopathological examination of infected tissues, typically the lamina propria of the intestine, where acid-fast staining has historically been used to demonstrate the presence of *M. avium* subsp. *paratuberculosis*, albeit with a low sensitivity and specificity (Thoresen et al. 1994. Comparison of immunohistochemistry, acid-fast staining, and cultivation for detection of *Mycobacterium paratuberculosis* in goats. J. Vet. Diagn. Investig. 6:195-199).

In view of the above, the need remains for improved diagnostic reagents for detecting and identifying *M. avium* subsp. *paratuberculosis*.

SUMMARY OF THE INVENTION

We have now discovered hybridoma cell lines which produce and secrete monoclonal antibodies which selectively bind to *Mycobacterium avium* subspecies *paratuberculosis*. Cells of *M. avium* subspecies *paratuberculosis* in biological samples may be detected and quantified by contacting the sample with the antibodies to form a *M. avium* subspecies *paratuberculosis*/antibody immunocomplex when *M. avium* subspecies *paratuberculosis* is present, which immunocomplex may then be detected. The monoclonal antibodies also may be incorporated into kits for the detection and quantification of *M. avium* subspecies *paratuberculosis*.

It is an object of this invention to provide hybridoma cell lines that produce and secrete high affinity monoclonal antibodies which selectively bind to *M. avium* subspecies *paratuberculosis*.

Another object of this invention is to provide hybridoma cell lines that produce and secrete monoclonal antibodies which selectively bind to cell surface proteins or membrane proteins of *M. avium* subspecies *paratuberculosis*.

A further object of this invention is to provide hybridoma cell lines that produce and secrete monoclonal antibodies which selectively bind to *M. avium* subspecies *paratuberculosis* and may be used in immunoassay methods for the measurement of *M. avium* subspecies *paratuberculosis* in biological samples.

Yet another object is to provide hybridoma cell lines that produce and secrete monoclonal antibodies which selectively bind to *M. avium* subspecies *paratuberculosis* and may be used for the purification and concentration of *M. avium* subspecies *paratuberculosis* from environmental or biological samples.

Other objects and advantages of this invention will become readily apparent from the ensuing description.

BRIEF DESCRIPTION OF THE FIGURES

FIG. 1 shows the localization of the epitopes of the MAb of Example 2 to regions of the MAP2121c gene product. Four constructs were produced and expressed in *E. coli*. The full-length protein and truncated versions of the protein are shown schematically. Protein sizes and relative positions within the full-length protein are depicted to scale based on the start and stop codons contained within the expression clone. Each of four quadrants of the protein can be distinguished based on MAb reactivity patterns.

DEPOSIT OF BIOLOGICAL MATERIALS

The hybridoma 14D4 is deposited under American Type Culture Collection (ATCC) Accession No. PTA-122026. The microorganism deposit was made under the provisions of the "Budapest Treaty on the International Recognition of the Deposit of Microorganisms for the Purposes of Patent Procedure". All restrictions on the availability to the public of these deposited microorganisms will be irrevocably removed upon issuance of a United States patent based on this application.

DETAILED DESCRIPTION OF THE INVENTION

In accordance with this invention we have created hybridoma cell lines that produce monoclonal antibodies that bind *M. avium* subspecies *paratuberculosis* and are effective for detecting and quantifying levels of this microorganism. The antibodies produced by these hybridomas of this invention may be used to rapidly and accurately detect and quantify *M. avium* subspecies *paratuberculosis*, providing an indicator of the level of this microorganism in biological samples. Alternatively, the antibodies produced by these hybridomas of this invention may be used for the purification and concentration of *M. avium* subspecies *paratuberculosis* from environmental or biological samples.

The hybridoma cell lines of this invention were produced by standard methods [Harlow and Lane (ed.). 1988. Antibodies: a laboratory manual. Cold Spring Harbor Laboratory Press, Cold Spring Harbor, N.Y.]. Briefly, BALB/c mice were immunized intraperitoneally three times at 14-day intervals with antigen derived from *M. avium* subspecies *paratuberculosis* (e.g., a sonicated protein lysate of cells or recombinant membrane proteins) suspended in PBS. The antigens were emulsified in Freund's incomplete adjuvant for all immunizations. The humoral immune responses of each mouse were evaluated by preparative immunoblot analysis with the antigen or culture supernatants. Splenic lymphocytes were recovered from the immunized mice and fused with continuously replicating SP2/0 myeloma cells, cultured, and screened. Positive antibody-secreting hybridomas were identified by immunoblot screening of hybridoma culture supernatants against *M. avium* subspecies *paratuberculosis* cell lysates or recombinant membrane protein, and stable secreting hybridomas were immunotyped to define heavy and light chains. Cross-reactivity with other mycobacteria was determined. From these screens, a total of nine hybridoma cell lines were retained as preferred for use herein: 17A12, 12C9, 14D4, 14G3, 14G11, 8G2, 13E1, 14C5, and 8G6. A detailed description of the techniques used for the production of the hybridoma cell lines in general is provided in the Examples.

Large quantities of the antibodies to *M. avium* subspecies *paratuberculosis* may be produced from the hybridoma cell lines in tissue culture using well-known techniques. In a preferred embodiment, the antibodies are produced in vitro in modular mini fermentors, as described by Falkenberg et al. (1995, J. Immunol. Methods, 179:13-29; and 1998, Res. Immunol., 149:560-570). Alternatively, antibodies may be produced within host animals, such as by ascites formation in syngenic mice. Monoclonal antibodies so produced may be purified, for example, by affinity chromatography on a protein A or G resin, or using cells or cell membranes of *M. avium* subspecies *paratuberculosis* bound to a resin.

The monoclonal antibodies produced in accordance with this invention possess high affinity for cells of *M. avium* subspecies *paratuberculosis*, allowing the rapid determination of this microorganism. Each of these antibodies react react with all *M. avium* subspecies *paratuberculosis* strains tested, including bovine isolate K-10, the type strain ATCC 19698, and the human isolate Linda. As described in detail in the Examples, all of the antibodies bind to and detect cell surface, cytoplasmic or membrane proteins of *M. avium* subspecies *paratuberculosis*. Specifically, monoclonal antibodies 12C9, 14D4, 14G3, and 14G11 all bind to an unidentified *M. avium* subsp. *paratuberculosis* protein that is primarily localized in the cell membrane fraction, monoclonal antibodies 8G2 and 13E1 bind to the major membrane protein encoded by MAP2121c of *M. avium* subsp. *paratuberculosis*, monoclonal antibodies 14C5, and 8G6 bind to the protein encoded by MAP1272c of *M. avium* subsp. *paratuberculosis*, and monoclonal antibody 17A12 binds to an as yet to be determined antigen of *M. avium* subsp. *paratuberculosis*. Cross-reactivity with other mycobacteria of the *M. avium* complex, while present with monoclonal antibodies 12C9, 14D4, 14G3, 14G11, 8G2, 13E1, 14C5, and 8G6, is somewhat variable between these antibodies. However, monoclonal antibody 17A12, is highly specific for *M. avium* subsp. *paratuberculosis* and is therefor particularly preferred. Monoclonal antibody 17A12, does not cross react with other mycobacteria, including other members of the *M. avium* complex, such as *M. avium* subspecies *silvaticum*, *M. avium* subspecies *avium* (tmc702), *M. scrofulaceum*, *M. abcessans*, *M. bovis*, *M. phlei*, *M. bovis* BCG, *M. avium* subspecies *avium* (tmc715) and *M. kansasii*. The isotype of preferred monoclonal antibody 17A12 is kappa light chain and IgG1 heavy chain.

The antibodies may be used to detect and/or quantify *M. avium* subspecies *paratuberculosis* in unknown samples using a variety of conventional immunosorbent assays including but not limited to RIA, FIA or ELISA. Moreover, the assays may be conducted using a single antibody, or multiple assays may be conducted using two or more of the antibodies having varying cross-reactivity for increased specificity to *M. avium* subspecies *paratuberculosis*. By way of example, in one specific embodiment, the microorganism may be detected using a competitive inhibition ELISA. In this assay, a sample to be analyzed is incubated with the monoclonal antibody for *M. avium* subspecies *paratuberculosis* and a solid substrate coated with cells of *M. avium* subspecies *paratuberculosis*, or cell membrane fragments, or cell-surface or membrane proteins recognized by the antibodies. The antigen coated substrate and any free cells of *M. avium* subspecies *paratuberculosis* in the sample thus compete for binding with the antibody. After incubation, the solid phase is drained and washed, and bound antibody on the substrate is detected and percent inhibition calculated. The concentration of *M. avium* subspecies *paratuberculosis* in the sample may then be determined by reference to a standard curve constructed from assays using known levels of *M. avium* subspecies *paratuberculosis*.

In one alternative embodiment, *M. avium* subspecies *paratuberculosis* may be determined by a competition ELISA such as described in Brandon et al. (U.S. Pat. No. 5,053,327, the contents of which are incorporated by reference herein) using the monoclonal antibody of the invention attached to a solid support. For example, the anti-*M. avium* subspecies *paratuberculosis* antibody may be immobilized on a solid support such as a bead or microtiter well. The unknown sample to be analyzed (or analytical standards of *M. avium* subspecies *paratuberculosis* or cell-surface or membrane proteins recognized by the antibodies) are then added with enzyme or radiolabeled *M. avium* subspecies *paratuberculosis*, and the amount of labeled *M. avium* subspecies *paratuberculosis* bound to the antibody is measured, using a substrate when the label is an enzyme. The amount of *M. avium* subspecies *paratuberculosis* in the sample is inversely proportional to the amount of bound labeled *M. avium* subspecies *paratuberculosis*. In another alternative, the monoclonal antibody may be attached to a solid support for use in conventional double-antibody sandwich ELISA procedures.

With any of the above-described assay formats, the monoclonal antibodies of the invention may be incorporated into kits, alone or preferably together with any other necessary reagents. A preferred kit for use herein comprises a first container including the monoclonal antibody, a second container including detection means effective for detecting bound antibody, and a solid phase support having cells of *M. avium* subspecies *paratuberculosis*, or cell membrane fragments, or cell-surface or membrane proteins or cytoplasmic proteins recognized by the antibodies attached thereto.

Determination of *M. avium* subspecies *paratuberculosis* in a variety of biological samples, including animal tissue and animal fluids such as serum, may be conducted using the above-described assays with minimal sample preparation and using simple extraction procedures. For the analysis of tissue samples, the tissue may be homogenized in buffer, such as Tris-HCl, centrifuged, and the liquid phase recovered and used directly in the immunoassay. Tissue for analysis in accordance with the invention may originate from virtually any animal. Without being limited thereto, the assays are preferably used for the analysis of tissue samples and fluids from domestic animals and wildlife, particularly bovine, caprine, and cervidae, and most particularly cattle, goats, and deer.

Another application of the monoclonal antibodies is affinity purification or concentration of *M. avium* subspecies *paratuberculosis*. The antibodies may be bound to a matrix, column, or other support using well-known techniques and used to recover or remove *M. avium* subspecies *paratuberculosis* from any desired material. Alternatively, the monoclonal antibodies may be incorporated into sensors such as solid phase electronic devices for detection of *M. avium* subspecies *paratuberculosis* in sample materials.

The following examples are intended only to further illustrate the invention and are not intended to limit the scope of the invention which is defined by the claims.

Example 1

The production of the hybridoma cell lines and their corresponding monoclonal antibodies described in this example are also disclosed in Bannantine et al. May, 2007. Development and Characterization of Monoclonal Antibodies and Aptemers against Major Antigens of *Mycobacterium avium* subsp. *paratuberculosis*. Clinical and Vaccine Immunology, 14(5):518-526, the contents of which are incorporated by reference herein.

Materials and Methods

Mycobacterial Antigens.

The National Animal Disease Center's mycobacterial culture collection served as the source of all strains used in this study (Table 1). *M. avium* subsp. *paratuberculosis* ATCC 19698 is the type strain; *M. avium* subsp. *paratuberculosis* Linda is a human isolate; and all other *M. avium* subsp. *paratuberculosis* strains tested are cattle isolates, including K-10, the sequenced strain (Li et al. 2005. The complete genome sequence of *Mycobacterium avium* subsp. *paratuberculosis*. Proc. Natl. Acad. Sci. USA 102:12344-12349). All mycobacteria were cultivated in Middlebrook 7H9 medium supplemented with oleic acid-albumin-dextrose-catalase (Hardy Diagnostics, Santa Maria, Calif.). For the cultivation of *M. avium* subsp. *paratuberculosis*, mycobactin J (2 mg/liter; Allied Monitor, Fayette, Mo.) was added to the Middlebrook-oleic acid-albumin-dextrose-catalase medium. The whole-cell-sonicated extracts of mycobacterial species and isolates were prepared for use as antigens in immunoassays, as described previously (Waters et al. 2003. Early induction of humoral and cellular immune responses during experimental *Mycobacterium avium* subsp. *paratuberculosis* infection of calves. Infect. Immun. 71:5130-5138). The sonicated extracts were centrifuged at 50,000×g for 1 h. The pellet was resuspended in an equal volume of phosphate-buffered saline (PBS; 150 mM NaCl, 10 mM $NaPO_4$, pH 7.4) and was thereafter used as the membrane-enriched fraction. The supernatant was collected and used as the cytosol-enriched fraction. All samples were assayed for protein content (Bio-Rad Laboratories [Richmond, Calif.] protein assay) and were stored at −20° C.

Expression clones producing recombinant *M. avium* subsp. *paratuberculosis* proteins were constructed by using the detailed methods described previously [Bannantine and Paustian. 2006. Identification of diagnostic proteins in *Mycobacterium avium* subsp. *paratuberculosis* by a whole genome analysis approach, p. 185-196. In L. O'Connor (ed.), Diagnostic bacteriology protocols, 2nd ed. Humana Press, Totowa, N.J.] and briefly mentioned below. All recombinant fusion proteins contained maltose-binding protein (MBP) as the tag for use in affinity purification. The MBP fusion was produced by cloning the *M. avium* subsp. *paratuberculosis* gene of interest into the pMAL-c2 expression vector (New England Biolabs, Beverly, Mass.). The entire reading frame or partial reading frame was amplified with AmpliTaq-Gold DNA polymerase (Applied Biosystems, Branchburg, N.J.) and purified *M. avium* subsp. *paratuberculosis* K-10 genomic DNA as the template. The upstream and downstream oligonucleotides for each amplification are listed in Table 2. The vector and amplification product were each digested with XbaI and HindIII and purified from 1% agarose gels with Gene Clean (Bio101). Ligation of these products yielded in-frame fusions between the malE gene in the vector and the *M. avium* subsp. *paratuberculosis* reading frame. After overnight ligation at 16° C., the products were transformed into competent *E. coli* cells (Invitrogen). Constructs from selected transformants in each experiment were authenticated by DNA sequencing. Each fusion protein was overexpressed and purified by maltose affinity chromatography by using an amylose resin supplied by New England Biolabs. The detailed methods used for the induction and affinity purification of MBP/MAP fusion proteins have been described previously (Bannantine and Paustian. 2006. ibid).

Production of MAbs.

MAbs were produced by standard methods [Harlow and Lane (ed.). 1988. Antibodies: a laboratory manual. Cold Spring Harbor Laboratory Press, Cold Spring Harbor, N.Y.]. Briefly, BALB/c mice were immunized intraperitoneally three times at 14-day intervals with a sonicated protein lysate of *M. avium* subsp. *paratuberculosis* K-10 (100 μg per injection) suspended in 0.5 ml of PBS (pH 7.3). The antigen was emulsified in Freund's incomplete adjuvant for all immunizations. The humoral immune responses of each mouse were evaluated by preparative immunoblot analysis with the sonicated antigen. Cell fusions with splenic lymphocytes and myeloma cells were performed with the cells from the best responder mouse. Positive antibody-secreting hybridomas were identified by immunoblot screening with culture supernatant. Stable secreting hybridomas were immunotyped by using isotype kit I from Pierce (Rockford, Ill.).

Immunoblot Assay.

Polyacrylamide gel electrophoresis (PAGE) was performed with 12% (wt/vol) polyacrylamide gels. Electrophoretic transfer of proteins onto pure nitrocellulose was accomplished with a Trans Blot Cell (Bio-Rad) with sodium phosphate buffer (25 mM, pH 7.8) at 0.8 A for 90 min. After transfer, the filters were blocked with PBS (pH 7.4) plus 2% bovine serum albumin (BSA) and 0.1% Tween 20, termed PBS-BSA. Culture supernatants or MAbs were diluted in PBS-BSA and exposed to the blot at room temperature for 2 h. After three washes in PBS plus 0.1% Tween 20, the blots were incubated for 1.5 h in goat anti-mouse peroxidase (Pierce) diluted 1:20,000 in PBS-BSA. The blots were again washed three times as described above and developed for chemiluminescence with SuperSignal detection reagents (Pierce). For preparative immunoblots, 12% SDS-polyacrylamide gels were cast with only a single lane (trough) across the top of the gel, in addition to a notch for the protein size standards. A 100-μl aliquot of *M. avium* subsp. *paratuberculosis* whole-cell protein lysate (0.1 mg total) was loaded into the single, long lane and the gel was subjected to electrophoresis. Blotting was then carried out as described immediately above. The complete panel of MAbs was evaluated on preparative immunoblots placed in a slot-blot device (Bio-Rad), such that individual culture supernatants could be loaded into independent slots on the same blot. This method enabled the most direct comparison of the antigen sizes detected by the respective MAbs.

Epitope Mapping of Selected Recombinant Proteins.

The full-length proteins of MAP1643 (AceAb) and MAP3840 (DnaK) as well as the N-terminal and C-terminal halves of each were produced as a fusion with MBP by the method described under "Mycobacterial antigens" above. The primers for these truncated and full-length constructs are shown in Table 2. These recombinant proteins were used in immunoblot analysis to determine if the location of antibody binding was at the N-terminal or the C-terminal half of each protein.

Electron Microscopy.

All fixation and staining procedures were conducted at room temperature. Mycobacterial bacilli were fixed for 2 to 4 h in 2.5% glutaraldehyde in 0.1 M cacodylate buffer, pH 7.4. Fixed cells were washed in the same buffer three times and were postfixed in 1% OsO4 in 0.1 M cacodylate buffer, pH 7.4, for 2 h. After the cells were washed in the same buffer, they were incubated with 30% ethanol for 10 min. The cells were further dehydrated with a graded series of ethanol and embedded in epoxy resin (Embed 812). Ultrathin sections for immunoelectron microscopy were washed in buffer three times for 15 min each time and etched with saturated sodium metaperiodate for 15 min. The cells were then blocked with 5% BSA for 30 min at room temperature. The cells were treated with each MAb (diluted 1:40) in the blocking solution for 2 h at room temperature. The cells were washed in Tris buffer containing 0.1% Tween 20 and 0.1% BSA four times for 10 min each time and were then incubated with goat anti-mouse immunoglobulin G (IgG) conjugated to colloidal gold (diameter, 10 nm) in Tris buffer for 2 h. The immunolabeled sections were washed in Tris buffer four times and fixed with 1% glutaraldehyde in Tris for 10 min. All ultrathin sections were double stained with uranyl acetate and Reynolds lead citrate and then observed under a Philips 410 microscope.

Results

MAbs Against *M. avium* Subsp. *Paratuberculosis* Whole-Cell Homogenates.

To obtain MAbs against *M. avium* subsp. *paratuberculosis* proteins, 6-week-old female BALB/c mice were immunized with a sonicated protein lysate of *M. avium* subsp. *paratuberculosis* K-10, as described in Materials and Methods. Ten hybridomas were identified by using this immunization regimen. By immunoblot analysis, the hybridomas reacted with a variety of proteins of different sizes from approximately 25 kDa to 85 kDa. However, the MAbs designated 11F6 and 9G10 each reacted with a protein of a similar size at approximately 85 kDa, and MAbs 13A4 and 11G4 also reacted with a similarly sized protein at approximately 66 kDa. MAb 5A10 initially reacted with a single band in the 45-kDa region; however, a subsequent tissue culture supernatant obtained from this hybridoma showed no reactivity, indicating that this hybridoma had stopped secreting antibody. The rest of the culture supernatants reacted strongly with a single, well-defined band or two bands. Because MAb 5A10 was not a stably secreting hybridoma, only the remaining nine MAbs were used in further experiments. A preliminary characterization of each stable MAb was performed by defining the isotype and antigen size. The isotype specificity of each MAb is presented in Table 3, along with the estimated size of the *M. avium* subsp. *paratuberculosis* proteins to which they bind.

Identification of *M. avium* Subsp. *Paratuberculosis* Antigens that Bind to Selected MAbs.

Several MAbs were obtained from mice immunized with a whole-cell homogenate of *M. avium* subsp. *paratuberculosis*. However, the *M. avium* subsp. *paratuberculosis* antigens that react with these MAbs are unknown. Therefore, four of the MAbs were used to screen an *M. avium* subsp. *paratuberculosis* lambda phage expression library developed previously (Bannantine and Stabel. 2001. Identification of two *Myco-*

*bacterium avium* subsp. *paratuberculosis* gene products differentially recognized by sera from rabbits immunized with live mycobacteria but not heat-killed mycobacteria. J. Med. Microbiol. 50:795-804). No positive plaques were obtained with MAbs 12C9 and 14G3; however, positive plaques were obtained when the library was screened with MAbs 11G4 and 9G10. DNA sequencing of the subcloned lambda phage inserts revealed open reading frames for MAP3840 (dnaK) and MAP1643 (aceAb) that reacted with MAbs 11G4 and 9G10, respectively. In order to conclusively demonstrate that these two MAbs reacted with the identified gene products, the MAP3840 and MAP1643 coding sequences were cloned and expressed in *Escherichia coli*. The purified recombinant fusion proteins representing MAP3840 and MAP1643 were analyzed by immunoblotting, which showed that these gene products were detected by the MAbs. AceAb is a probable isocitrate lyase enzyme that is involved in the glyoxylate cycle (Honer Zu Bentrup et al. 1999. Characterization of activity and expression of isocitrate lyase in *Mycobacterium avium* and *Mycobacterium tuberculosis*. J. Bacteriol. 181: 7161-7167). DnaK is the 70-kDa heat shock protein (Young and Garbe. 1991. Heat shock proteins and antigens of *Mycobacterium tuberculosis*. Infect. Immun. 59:3086-3093). Mapping multiple MAbs to MAP3840 and MAP1643.

Once the identities of the antigens that reacted with MAbs 9G10 and 11G4 were discovered, further experimentation quickly revealed that additional independently isolated MAbs, 13A4 and 11F6, also detected MAP3840 and MAP1643, respectively (Table 3). One-dimensional sodium dodecyl sulfate (SDS)-PAGE separation of the fractionated lysates, followed by excision and mass spectroscopy of prominent Coomassie blue-stained bands, showed that both the MAP3840 and the MAP1643 gene products were present in high relative abundance in *M. avium* subsp. *paratuberculosis* (data not shown). Therefore, because of the antigenicity and high relative abundance of the MAP1643 and the MAP3840 gene products, it was not surprising to obtain multiple MAbs to these proteins. To determine if these MAbs detected the same epitopes or distinct epitopes within the same protein, the N-terminal and C-terminal halves of each protein were cloned and purified from the recombinant *E. coli* cells. These proteins, along with the corresponding full-length proteins, were then analyzed by immunoblotting with each of the respective MAbs. Both MAb 11F6 and MAb 9G10 bound to the C-terminal half of AceAb. Furthermore, MAb 11G4 detected the N-terminal half of DnaK, but MAb 13A4 detected only the full-length protein. These data suggest that MAbs 11G4 and 13A4 may bind to distinct epitopes within DnaK; however, because MAbs 11F6 and 9G10 both bound to the C-terminal half of AceAB, it remains inconclusive if the epitope is shared or distinct.

Specificities of Antimycobacterial MAbs.

Antibodies were next screened by immunoblotting with whole-cell lysate preparations of nine mycobacterial species and subspecies, including *M. avium* subsp. *avium, M. avium* subsp. *silvaticum, M. avium* subsp. *paratuberculosis, M. scrofulaceum, M. abscessus, M. bovis, M. phlei, M. intracellulare*, and *M. kansasii*. All nine stable MAbs reacted to all three of the *M. avium* subsp. *paratuberculosis* isolates, which included K-10; ATCC 19698; and isolate Linda, which was recovered from a patient with Crohn's disease. Although the MAb 11F6 immunoblot is not shown, reactivity identical to that observed for MAbs 9G10 and 14G11 was obtained by using this MAb. MAb 14D4 showed the most unexpected immunoblot reactivity, with bands of widely varying sizes detected among the different mycobacterial species. Surprisingly, MAb 14D4 was also the only antibody that did not detect either of the *M. avium* subsp. *avium* isolates but reacted with the more distantly related mycobacteria, such as *M. phlei* and *M. bovis*. While all antibodies showed some degree of cross-reactivity with other mycobacterial species, MAb 12C9 showed strong reactivity with the two *M. avium* subsp. *paratuberculosis* bovine isolates and weaker reactivity with Crohn's disease isolate Linda. The 4B6 antibody detected a protein that was the most conserved among the mycobacteria, as a band of similar size was observed in every species and subspecies tested.

Location of *M. avium* Subsp. *Paratuberculosis* Antigens that Bind to MAbs.

Antigen localization was determined by immunoblot analysis of the MAbs against membrane-enriched and cytosol-enriched fractionated lysates, prepared as described in Materials and Methods. Note that MAbs 12C9, 14D4, 14G3, and 14G11 all bound to an unidentified *M. avium* subsp. *paratuberculosis* protein that is primarily localized in the cell membrane fraction, whereas MAbs 4B6, 9G10, and 11G4 and MAbs 11F6 and 13A4 all detected proteins that were present predominantly in the cytoplasmic fraction. The protein detected by MAb 14G3 may form a dimer complex in the membrane-enriched fraction, as a protein band approximately twice the size of the monomer was also detected.

Detection of *M. avium* Subsp. *Paratuberculosis* Bacilli by Immunoelectron Microscopy with the MAbs Developed in this Example.

Each of the MAbs was next evaluated to determine reactivity levels with mycobacterial bacilli by immunoelectron microscopy. Of all the MAbs tested, MAbs 14D4 and 9G10 showed the most immunogold labeling, which indicates antibody binding to *M. avium* subsp. *paratuberculosis*. Although MAb 4B6 reacted strongly with all mycobacteria tested by immunoblotting, no reactivity by immunoelectron microscopy was observed, suggesting that either the processing for microscopy damaged the epitope or the epitope is perhaps masked by another protein(s). None of the labeling patterns were distinct enough to confirm the subcellular locations of the antigens to which they bind, although MAb 14D4 seemed to label mostly at the periphery of the bacilli. This labeling pattern is consistent with what was observed by immunoblotting of the fractionated lysates probed with MAb 14D4.

Development of Aptamers to the *M. avium* Subsp. *Paratuberculosis* Hypothetical Protein Encoded by MAP0105c.

In an attempt to obtain a more specific reagent to detect *M. avium* subsp. *paratuberculosis*, aptamers were screened to identify those that bind to the MAP0105c gene product recombinantly produced in *E. coli*. Aptamers are short nucleic acid sequences that bind to specific protein epitopes with a high affinity (Proske et al. 2005. Aptamers-basic research, drug development, and clinical applications. Appl. Microbiol. Biotechnol. 69:367-374). MAP0105c is a gene reported to be unique to *M. avium* subsp. *paratuberculosis* (Bannantine et al. 2002. Genome scale comparison of *Mycobacterium avium* subsp. *paratuberculosis* with *Mycobacterium avium* subsp. *avium* reveals potential, diagnostic sequences. J. Clin. Microbiol. 40:1303-1310). In that study, MAP0105c was designated gene 218, because the project was published prior to annotation of the *M. avium* subsp. *paratuberculosis* K-10 genome (Li et al. 2005. ibid). Three aptamers, designated 43, 93, and 94, were obtained following repeated screening and enrichments with the recombinant protein. Immunoblot analysis with these aptamers showed binding to the protein of the correct size, but reactivity was also seen in most of the mycobacteria analyzed. This cross-reactivity with other mycobacteria prompted a reexamination of MAP0105c by BLAST analysis. This analysis still suggested that the nucleotide sequence of MAP0105c is present only in *M. avium* subsp. *paratuberculosis* and not other bacteria, including mycobacteria; however, BLAST analysis with the translated sequence did show hits in *Streptomyces* (30% identity), *Frankia* (22% identity), and *Rhodococcus* (28% identity). MAP0105c was also produced as N-terminal and C-terminal halves (designated 218-4 and 218-9, respectively), and dot blot analysis with these truncated proteins shows that all three aptamers detected the N-terminal half. Furthermore, all aptamers reacted more strongly with the nondenatured recombinant protein than with the denatured recombinant protein.

DISCUSSION

The predominant difficulties in working with *M. avium* subsp. *paratuberculosis*—the slow growth, the underdeveloped technology for genetic modification, and the intramacrophage location during infection, combined with a lack of knowledge regarding the 1,810 *M. avium* subsp. *paratuberculosis* hypothetical and unknown proteins-present challenges that require unique approaches. The production of MAbs, such as those produced in this study, is one critical tool currently lacking in JD research. The absence of these reagents has blocked the progress of unique research approaches directed at controlling this disease.

All MAbs and aptamers produced in this study cross-reacted with one or more species of mycobacteria. This result is not surprising, given the high degree of genetic similarity that *M. avium* subsp. *paratuberculosis* shares with other members of the MAC complex (Paustian et al. 2005. Comparative genomic hybridizations reveal genetic regions within the *Mycobacterium avium* complex that are divergent from *Mycobacterium avium* subsp. *paratuberculosis* isolates. J. Bacteriol. 187:2406-2415), and highlights the challenges encountered in the development of subspecies-specific detection reagents for this pathogen. However, what is surprising is that MAb 14D4 did not react with *M. avium* subsp. *avium*, which is most closely related to *M. avium* subsp. *paratuberculosis*, and yet this same MAb reacted with the more distantly related species *M. bovis* and even *M. phlei*.

In an effort to obtain a more specific detection reagent for *M. avium* subsp. *paratuberculosis*, aptamers that bind to the MAP0105c gene product were obtained. Nucleic acid similarity searches and PCR surveys have previously suggested that this gene is present uniquely in *M. avium* subsp. *paratuberculosis* (Bannantine et al. 2002, ibid). The three aptamers identified in these studies all detected the N-terminal half of MAP0105c. However, aptamer 94 bound to nearly all mycobacteria tested, suggesting that MAP0105c has conserved epitopes. Because the aptamers clearly reacted with the *E. coli*-expressed fusion protein representing MAP0105c, we are confident that they bind specifically to the native MAP0105c protein produced by *M. avium* subsp. *paratuberculosis*. The unexpected cross-reactivity prompted a BLAST analysis of the nonredundant protein database with MAP0105c, which shows that the nucleic acid sequence is present uniquely in *M. avium* subsp. *paratuberculosis*; however, the translated sequence has similarity to a hypothetical protein from *Streptomyces avermitilis*, with a 30% amino acid identity, and a hypothetical protein from *Frankia* species (22% identity). Nonetheless, there is still no bioinformatic evidence to explain the cross-reactivity with other mycobacterial species observed in this study. Taken together, these results suggest that MAP0105c does have conserved epitopes and that at least sections of the gene product should not be considered *M. avium* subsp. *paratuberculosis* specific.

To identify the corresponding antigens, four MAbs were chosen and used to screen an *M. avium* subsp. *paratuberculosis* lambda phage expression library. It is interesting to note that only MAbs 11G4 and 9G10, both of which detected proteins present in the cytoplasm of *M. avium* subsp. *paratuberculosis*, were identified during the screening of the expression library. The other two MAbs, 12C9 and 14D4, used in the screening experiments reacted with proteins in the mycobacterial cell membrane fraction. It is likely that the membrane proteins detected by MAbs 12C9 and 14D4 are not readily cloned or expressed or are under represented in the lambda phage library. An alternative strategy that could be used to identify these membrane proteins is to combine affinity purification with the MAbs to capture the native *M. avium* subsp. *paratuberculosis* protein and analyze the antibody-antigen complex by tandem mass spectroscopy. This method would enable limited sequence identification of the peptides from the captured antigen, thus overcoming cloning and, expression obstacles.

Heat shock proteins, which belong to families of widely conserved proteins found in prokaryotes and eukaryotes, are commonly immunodominant antigens recognized following infection with many bacterial pathogens (Ausiello et al. 2005. 60-kDa heat shock protein of *Chlamydia pneumoniae* is a target of T-cell immune response. J. Biol. Regul. Homeost. Agents 19:136-140; Koets et al. 2006. Mycobacterial 70 kD heat-shock protein is an effective subunit vaccine against bovine *paratuberculosis*. Vaccine 24:2550-2559; Koets et al. 2001. Differential changes in heat shock protein-, lipoarabinomannan-, and purified protein derivative-specific immunoglobulin G1 and G2 isotype responses during bovine *Mycobacterium avium* subsp. *paratuberculosis* infection. Infect. Immun. 69:1492-1498; and Zugel and Kaufmann. 1999. Immune response against heat shock proteins in infectious diseases. Immunobiology 201:22-35). The *M. avium* subsp. *paratuberculosis* DnaK, encoded by MAP3840, appears to be immunodominant as well, since two of nine immortalized B-cell cultures secreting antibody to this protein were obtained. While this cytoplasmically located antigen is not unique to *M. avium* subsp. *paratuberculosis*, it is present in high relative abundance in mycobacterial bacilli cultured in Middlebrook 7H9 medium, which may also account for the identification of more than one MAb. The same is also true for AceAb, encoded by MAP1643.

Although aceAb is considered a metabolic gene encoding the isocitrate lyase enzyme used in the glyoxylate cycle, it has been shown to be upregulated in *M. avium* subsp. *avium*-infected macrophages (Sturgill-Koszycki et al. 1997. The interaction between *Mycobacterium* and the macrophage analyzed by two-dimensional polyacrylamide gel electrophoresis. Electrophoresis 18:2558-2565), implicating it in virulence as well. In *M. tuberculosis* H37Rv, the isocitrate lyase gene actually consists of two overlapping genes (aceAa at 1,104 bp and aceAb at 1,197 bp) that share a single base pair at the 3' end of aceAa and the 5' end of aceAb but is a single 2,300-bp gene in *M. tuberculosis* CDC1551 (Fleischmann et al. 2002. Whole-genome comparison of *Mycobacterium tuberculosis* clinical and laboratory strains. J. Bacteriol. 184:5479-5490). In *M. avium* subsp. *paratuberculosis*, aceAb appears to be a single open reading frame 2,289 bp in length sandwiched by two hypothetical genes, MAP1642 and MAP1644 (Li et al. 2005, ibid).

As an initial step in defining the antigenic structure of DnaK and AceAb, the epitopes were mapped to either the N-terminal or the C-terminal halves of the proteins. Both MAbs 11F6 and 9G10 detected the C-terminal half of AceAb, suggesting that this half may contain more B-cell epitopes or perhaps a single dominant epitope. In contrast, MAb 11G4 detected the N-terminal half of DnaK, while MAb 13A4 did not react with either half of DnaK and detected only the full-length protein. These data suggest that MAbs 11G4 and 13A4 recognize distinct epitopes. The exact reason why MAb 13A4 detects only the full-length protein is unclear; however, one possibility is that the epitope is at the center of the protein and that by producing the two halves, the epitope is no longer intact. A more likely possibility is that the MAb detects a conformational or discontinuous epitope that is disrupted when only one half of the protein is represented.

From this study, four MAbs that react with proteins present in the membrane fraction of *M. avium* subsp. *paratuberculosis* were identified. Thus, these proteins may even be surface exposed and, hence, immune targets for the host. Although these potential surface proteins remain to be identified, the MAbs are nonetheless useful in many applications. Pathogenesis studies should include MAbs that bind to surface molecules because they may block infection of cultured epithelial cells (Bannantine et al. 2003. The *Mycobacterium avium*. subsp. *paratuberculosis* 35 kDa protein plays a role in invasion of bovine epithelial cells. Microbiology 149:2061-2069) or facilitate uptake and entry into macrophages (Hostetter et al. 2005. Opsonization effects on *Mycobacterium avium* subsp. *paratuberculosis*-macrophage interactions. Clin. Diagn. Lab. Immunol. 12:793-796). The results from these studies would determine if the proteins are important in adherence or invasion of epithelial cells that line the bovine or ovine intestine. More practically, these novel MAbs may be used to purify and concentrate *M. avium* subsp. *paratuberculosis* from environmental samples, such as water or bulk milk tank samples, by immunomagnetic separation technologies (Metzger-Boddien et al. 2006. Automated high-throughput immunomagnetic separation-PCR for detection of *Mycobacterium avium* subsp. *paratuberculosis* in bovine milk. Int. J. Food Microbiol. 110:201-208; Whan et al. 2005. Development of an IMS-PCR assay for the detection of *Mycobacterium avium* ssp. *paratuberculosis* in water. Lett. Appl. Microbiol. 40:269-273). Confident identification of *M. avium* subsp. *paratuberculosis* in tissues from Crohn's disease patients might also be obtained with these MAbs. Furthermore, the MAbs developed in this study can be used to identify the potential surface proteins on *M. avium* subsp. *paratuberculosis*, making them strong candidates for subunit vaccines. Finally, they also provide a way to check the quality of fractionated protein preparations, such as membrane-enriched or cytoplasm-enriched lysates used in proteomic studies.

It is important to have MAbs against proteins that are located on the cell surface or cell membrane for ease of *bacillus* detection in downstream applications. While MAbs to a cytoplasmic protein may be important in studies highly focused on particular proteins, they may not be as effective at detecting bacilli in diagnostic or general research settings. Not all MAbs are used solely for detection purposes, however. Further delineation of the epitopes recognized by both antibodies as well as T cells will be important in understanding the immunopathological conditions caused by infection with *M. avium* subsp. *paratuberculosis*. The MAbs described here may be extremely useful reagents for such studies.

Example 2

The production of the hybridoma cell lines and their corresponding monoclonal antibodies described in this example are also disclosed in Bannantine et al. March, 2007. Production and Characterization of Monoclonal Antibodies against a Major Membrane Protein of *Mycobacterium avium* subsp. *paratuberculosis*. Clinical and Vaccine Immunology, 14(3): 312-317, the contents of which are incorporated by reference herein.

Materials and Methods

The mycobacterial strains used in this Example were the same as described in Example 1. All mycobacteria were cultivated in Middlebrook 7H9 medium supplemented with OADC (Hardy Diagnostics, Santa Maria, Calif.). All strains were cultivated, and whole-cell sonicated extracts were prepared for use as antigens in immunoassays as described in Example 1. Membrane-enriched and cytosol-enriched fractionated lysates were prepared as described previously (Radosevich et al. 2007. Proteome and differential expression analysis of membrane and cytosolic proteins from *Mycobacterium avium* subsp. *paratuberculosis* strains K-10 and 187. J. Bacteriol. 189:1109-1117).

Expression clones producing recombinant *M. avium* subsp. *paratuberculosis* proteins were obtained using methods previously described in detail (Bannantine and Paustian, 2006, ibid). All recombinant fusion proteins contained maltose-binding protein (MBP) as the tag used in affinity purification. For cloning, the full-length gene was amplified using 2121c-F and 2121c-R primers (Table 4) whereas primers 2121c-F and 2121c-N-R were used to amplify the 5' half and primers 2121c-C-F and 2121c-R were used to amplify the 3' end. The central segment of the MAP2121c open reading frame was amplified using 2121c-CenF and 2121c-CenR. Details of the methods used for the induction and affinity purification of MBP-MAP2121c gene product fusion proteins have been described previously (Bannantine and Paustian, 2006, ibid).

Monoclonal antibodies were produced using standard methods (Harlow and Lane, ibid). Briefly, 6-week-old female BALB/c mice were immunized three times intraperitoneally with the recombinant fusion protein (100 µg per injection) suspended in 0.5 ml of phosphate-buffered saline (PBS; pH 7.3) at 14-day intervals. The antigen was emulsified in incomplete Freund adjuvant (Sigma, St. Louis, Mo.). Antigen-specific-antibody-secreting hybridomas were identified by preparative immunoblot screening of the recombinant protein against culture supernatants. Each well containing tissue culture supernatant was used to probe two preparative immunoblots, one containing the recombinant fusion protein and a second containing the MBP affinity tag alone. This process enabled the identification of those antibodies that reacted specifically with MMP and not the affinity purification tag. mAbs were immunotyped using isotype kit I (Pierce, Rockford, Ill.) to define the heavy and light chains.

Polyacrylamide gel electrophoresis was performed using 12% (wt/vol) polyacrylamide gels or 4 to 12% NuPage precast gels (Invitrogen) run with MOPS (morpholinepropanesulfonic acid) buffer (Invitrogen) to resolve membrane-enriched and cytoplasm-enriched fractions. Polyacrylamide gels were stained with GelCode Blue (Pierce). Either Precision Plus protein standards (Bio-Rad) or SeaBlue Plus2 prestained standards (Invitrogen) served as size references for protein gels. The electrophoretic transfer of proteins onto pure nitrocellulose and the immunoblot assays were accomplished as described previously (Paustian et al. 2004. Characterization of novel coding sequences specific to *Mycobacterium avium* subsp. *paratuberculosis*: implications for diagnosis of Johne's Disease. J. Clin. Microbiol. 42:2675-2681). mAb 8G2 was diluted 1:1,000 and mAb 13E1 was diluted 1:500 routinely for experiments described herein.

*Mycobacterium*-infected BoMac cells were cultured in sterile glass chamber slides (Nalgene Nunc International, Naperville, Ill.) for 48 h and fixed in 100% methanol as described previously (Bannantine and Stabel, 2001, ibid). Multiplicities of infection were five mycobacteria to one macrophage. Fixed cells were washed in PBS following the 5-min methanol fixation and stored at 4° C. in PBS until ready to use. Fixed cells were blocked in PBS plus 2% (wt/vol) bovine serum albumin (PBS-BSA). Each monoclonal antibody was diluted in PBS-BSA as indicated above for immunoblot experiments and placed on the chamber slide for 1 h. The slide was washed three times with PBS, and primary antibodies were detected with Alexa Fluor 488-conjugated goat anti-mouse immunoglobulin G (Invitrogen) at a dilution of 1:500 in PBS-BSA. The slide was incubated at room temperature in the dark for 1 h and then washed again three times with PBS. Excess PBS was drained away, and the slide was prepared for microscopy with a drop of Vectashield mounting medium containing 4',6'-diamidino-2-phenylindole (DAPI; Vector Laboratories, Burlingame, Calif.) and a coverslip. Labeled cells were visualized by differential interference contrast (DIC) and fluorescence microscopy with a Nikon E800 series microscope.

Results

An *M. avium* subsp. *paratuberculosis* protein encoded by MAP2121c was previously shown to play a role in the invasion of epithelial cells (Bannantine et al. 2003. ibid). The protein was heterologously expressed as a full-length fusion protein in *Escherichia coli* to serve as an antigen. To obtain MAbs against MMP, BALE/c mice were immunized with the recombinant fusion protein. The fusion of immune splenocytes with SP2/0 myeloma cells resulted in six hybridomas initially testing positive in immunoblot screens, but only two stable cell lines secreting antibody to MMP were obtained, and these antibodies were designated 8G2 and 13E1.

Supernatants from the 8G2- and 13E1-secreting cell lines were evaluated by immunoblotting with the recombinant protein expressed in *E. coli* as well as whole-cell lysates of *M. avium* subsp. *paratuberculosis*. Both 8G2 and 13E1 detected a 35-kDa protein in *M. avium* subsp. *paratuberculosis* as well as the *E. coli*-expressed recombinant MBP-MAP2121c fusion protein. However, neither antibody detected the MBP-LacZ fusion protein, suggesting that neither MAb reacts with the affinity tag. As a control, a third immunoblot was probed with a MAb that binds to the MBP affinity tag. This antibody, developed in our laboratory during this study, detected both MBP-LacZ and MBP-MAP2121c gene product fusion proteins, but nothing was detected in *M. avium* subsp. *paratuberculosis* whole-cell lysates. Isotype analysis revealed that both 8G2 and 13E1 MAbs were immunoglobulin G1 heavy-chain and kappa light-chain antibodies.

Because the MAP2121c coding sequence is present in other mycobacteria, the cross-reactivities of 8G2 and 13E1 were determined. Each MAb was screened by immunoblotting with whole-cell lysate preparations from nine mycobacterial species and subspecies. Both MAbs reacted to all three *M. avium* subsp. *paratuberculosis* strains, which included K-10 and the type strain, ATCC 19698, as well as a human isolate. 13E1 detected a similarly sized protein in all members of the *M. avium* complex, which includes *M. avium* subsp. *avium*, *M. avium* subsp. *silvaticum* (Jorgensen et al. 1976. Mycobacteriosis in a roe-deer caused by wood-pigeon mycobacteria. Nord. Vet. Med. 28:539-546), *M. avium* subsp. *paratuberculosis*, and *M. intracellulare*. Similar reactivity of 8G2 with *M. avium* complex members was observed; however, the epitope detected by this MAb may be more conserved than the one recognized by 13E1 as 8G2 also cross-reacts with *M. abscessus* and *M. kansasii*. A smaller protein than the MMP produced in *M. avium* complex mycobacteria was detected in those two species. Neither MAb detected any proteins in *M. scrofulaceum*, *M. bovis*, or *M. phlei*.

Figure 1:
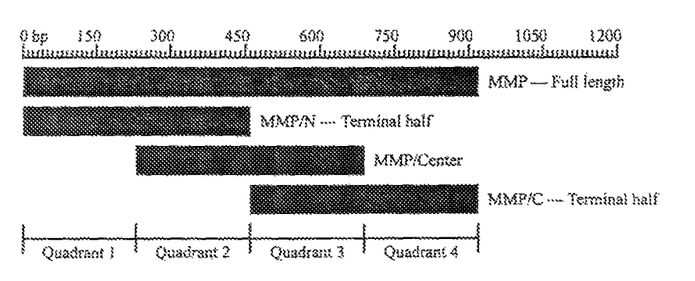

The results of specificity experiments, which showed distinct patterns of reactivity among the mycobacterial species, suggested that 8G2 and 13E1 may bind distinct epitopes within MMP. To determine if this hypothesis was true, fragments of the MAP2121c gene encoding the N-terminal, center, and C-terminal regions of the protein were cloned and expressed and the truncated proteins were purified from recombinant *E. coli* cells. The regions spanned by these truncated versions of MMP relative to full-length MMP are shown schematically to scale in FIG. 1. The full-length gene is 924 bp, encoding a protein encompassing 307 amino acids. The MMP N-terminal truncation included the initial 154 amino acids, and the MMP C-terminal truncation included the final 153 amino acids. The MMP center truncation included the central 155 amino acids. These constructs were designed such that the epitopes could be quickly mapped to four specific quadrants within the protein as shown in FIG. 1. These proteins, along with the corresponding full-length protein, were then analyzed by immunoblotting with each of the respective MAbs. Data show that, in addition to the full-length protein, 8G2 binds strongly to the N-terminal end as well as to the central region of MMP. This reactivity pattern suggests that the epitope lies within a 77-amino-acid region of overlap between the MMP N-terminal and center polypeptides (quadrant 2 in FIG. 1). MAb 13E1 detected only the full-length protein. This experiment was repeated with poly-histidine-tagged recombinant fusion proteins, and the same results were obtained. These data confirm that 8G2 and 13E1 recognize distinct epitopes within MMP and suggest that 13E1 may recognize either a very large linear or a conformational epitope that is disrupted in the truncated versions of MMP.

Antigen localization was performed by immunoblot analysis of cell-fractionated lysates prepared from five *M. avium* subsp. *paratuberculosis* isolates. MAb 8G2 showed that MMP was present predominantly within the membrane-enriched fraction, although some reactivity in the cytoplasm-enriched fractions was observed. Results similar to that shown for 8G2 were also obtained using 13E1.

A major obstacle in defining more precisely the role of MMP in the pathogenesis of Johne's disease is the lack of reagents that would facilitate the specific immunodetection of MMP. To determine if these mAbs might be useful in detecting *M. avium* subsp. *paratuberculosis* within infected macrophages, an indirect immunofluorescence assay was performed. Bovine macrophages immortalized with simian virus 40 (Stabel and Stabel. 1995. Immortalization and characterization of bovine peritoneal macrophages transfected with SV40 plasmid DNA. Vet. Immunol. Immunopathol. 45:211-220) were infected with *M. avium* subsp. *paratuberculosis* and fixed in methanol 48 h postinfection. Intracellular bacilli stained equally well with Alexa Fluor 488-labeled 13E1 and 8G2. In contrast, no staining with Alexa Fluor 488-labeled 13E1 and 8G2 in neighboring uninfected cells was observed, although cells labeled with 8G2 showed a very slight increase in background fluorescence relative those labeled with 13E1.

These MAbs described herein are the first described MAbs that detect a known *M. avium* subsp. *paratuberculosis* membrane protein. Membrane proteins are commonly immunodominant antigens recognized following infection with any of numerous bacterial pathogens (Darji et al. 1998. The role of the bacterial membrane protein ActA in immunity and protection against *Listeria monocytogenes*. J. Immunol. 161: 2414-2420; Podmore e al. 2001. Immunodominant antigens in periodontal disease: a real or illusive concept? Crit. Rev. Oral Biol. Med. 12:179-185). While the *M. avium* subsp. *paratuberculosis* genome sequence has revealed a few hundred putative cell membrane proteins, using antibodies developed in this study, we were able to confirm experimentally that MMP is a surface protein in all five isolates tested. MMP has been reported to be immunodominant in patients with leprosy (Triccas et al. 1998. Specific serological diagnosis of leprosy with a recombinant *Mycobacterium leprae* protein purified from a rapidly growing mycobacterial host. J. Clin. Microbiol. 36:2363-2365; Triccas et al. 1996. A 35-kilodalton protein is a major target of the human immune response to *Mycobacterium leprae*. Infect. Immun. 64:5171-5177). Although a previous study using immunoblotting found that this protein also shows reactivity with samples from cattle with Johne's disease (Bannantine et al. 2003, ibid), only 13 cows were clinically evaluated in that study. Therefore, more extensive studies are needed to further assess the immunodominance of this protein in the context of Johne's disease.

Both antibodies label intramacrophage bacilli for visualization by immunofluorescence microscopy suggesting that these antibodies should work for immunohistochemistry with infected tissues as well.

For quickly mapping the epitopes of MMP, three truncated recombinant MMP proteins were produced in addition to the full-length protein. Although the precise epitopes for each mAb were not defined at a high resolution by using synthetic overlapping peptides (Mechin et al. 1996. Identification of surface-exposed linear B-cell epitopes of the nonfimbrial adhesin CS31A of *Escherichia coli* by using overlapping peptides and antipeptide antibodies. Infect. Immun. 64:3555-3564), the production of truncated versions of MMP clearly showed that 8G2 and 13E1 recognize distinct epitopes. The 8G2 epitope mapped to a 77-amino-acid region on the N-terminal half of MMP, whereas 13E1 detected the full-length protein but none of the truncated proteins. It is unknown why 13E1 detects only the full-length protein; however, one possibility is that the mAb detects a discontinuous epitope formed by the natural aggregation or folding of the—and C-terminal sections that is disrupted when one section of the protein is missing. The reducing agent 2-mercaptoethanol apparently does not disrupt this conformational epitope as it is detected by immunoblotting. In addition, if conformational changes in MMP do occur by bringing each end of the protein together, this may explain why the truncated MMP observed in *M. kansasii* and *M. abscessus* may not be detected by 13E1, because one end may be missing in the MMP produced by those species. Regardless of the possible explanation, it is clear that distinct epitopes within MMP are recognized by the two MAbs.

From the immunoblot experiments with several mycobacterial species, it can be concluded that 13E1 is specific for the *M. avium* complex, comprising *M. intracellulare* and the three subspecies of *M. avium* (Inderlied et al. 1993. The *Mycobacterium avium* complex. Clin. Microbiol. Rev. 6:266-310; Thorel et al. 1990. Numerical taxonomy of mycobactin-dependent mycobacteria, emended description of *Mycobacterium avium*, and description of *Mycobacterium avium* subsp. *avium* subsp. nov., *Mycobacterium avium* subsp. *paratuberculosis* subsp. nov., and *Mycobacterium avium* subsp. *silvaticum* subsp. nov. Int. J. Syst. Bacteriol. 40:254-260). However, the finding that 8G2 recognized MMP in *M. kansasii* provides evidence of determinants shared between this species and members of the *M. avium* complex. This cross-reactivity was also observed with *M. abscessus*, which was previously classified as *M. chelonae* (Kusunoki and Ezaki. 1992. Proposal of *Mycobacterium peregrinum* sp. nov., nom. rev., and elevation of *Mycobacterium chelonae* subsp. *abscessus* (Kubica et al.) to species status: *Mycobacterium abscessus* comb. nov. Int. J. Syst. Bacteriol. 42:240-245). The detection of MMP in *M. abscessus* was surprising as this species is a fast-growing *mycobacterium* that is distantly related to the *M. avium* complex (Devulder et al. 2005. A multigene approach to phylogenetic analysis using the genus *Mycobacterium* as a model. Int. J. Syst. Evol. Microbiol. 55:293-302). *M. kansasii* is more closely related to the *M. avium* complex than *M. bovis* and more distantly related than *M. scrofulaceum* (Devulder et al. 2005. ibid), yet paradoxically, antibodies did not react with any protein in *M. bovis* or *M. scrofulaceum*.

It is noteworthy that a smaller protein than the MMP produced by members of the *M. avium* complex was detected in both *M. kansasii* and *M. abscessus*. It is unclear whether the decreased size is due to proteolytic processing or if it is simply a natural truncation in these more distantly related species. Bioinformatic analysis of the MAP2121c gene product does not reveal any type of signal peptidase cleavage sequence normally associated with membrane-targeted proteins; however, it is unknown whether *M. kansasii* or *M. abscessus* may have such a cleaved signal sequence, which may account for the smaller size. An insertion sequence in the MAP2121c gene of *M. avium* subsp. *paratuberculosis* and corresponding orthologs in *M. avium* complex members seem unlikely as no similarity to any known insertion sequence elements appears upon BLAST analysis.

The MAbs described herein are useful for detection by immunofluorescence microscopy, making them useful in cell biology and pathogenesis studies. Although not subspecies specific, these MAbs nonetheless have potential clinical use as immunodiagnostic reagents for histopathology (Coetsier et al. 1998. Detection of *Mycobacterium avium* subsp. *paratuberculosis* in infected tissues by new species-specific immunohistological procedures. Clin. Diagn. Lab. Immunol. 5:446-451), sandwich enzyme-linked immunosorbent assays, and general research applications. They may be of particular importance for experimental or epidemiologic studies with samples in which enrichment with *M. avium* subsp. *paratuberculosis* among high levels of other environmental bacteria is beneficial (Berger et al. 2006. ibid). Such samples include water (Whan et al. 2005. ibid) and bulk milk tank (Grant et al. 2000. Improved detection of *Mycobacterium avium* subsp. *paratuberculosis* in milk by immunomagnetic PCR. Vet. Microbiol. 77:369-378; O'Reilly et al. 2004. Surveillance of bulk raw and commercially pasteurized cows' milk from approved Irish liquid-milk pasteurization plants to determine the incidence of *Mycobacterium paratuberculosis*. Appl. Environ. Microbiol. 70:5138-5144) samples as well as other environmental samples (Berghaus et al. 2006. Environmental sampling for detection of *Mycobacterium avium* ssp. *paratuberculosis* on large California dairies. J. Dairy Sci. 89:963-970; Raizman et al. 2004. The distribution of *Mycobacterium avium* ssp. *paratuberculosis* in the environment surrounding Minnesota dairy farms. J. Dairy Sci. 87:2959-2966).

It is understood that the foregoing detailed description is given merely by way of illustration and that modifications and variations may be made therein without departing from the spirit and scope of the invention.

TABLE 1

Mycobacterial isolates used in this study

| Isolate | Organism | Host | Location | Reference or source |
|---|---|---|---|---|
| K-10 | M. avium subsp. paratuberculosis | Bovine | Feces | 20 |
| 19698 | M. avium subsp. paratuberculosis | Bovine | Feces | ATCC 19698 |
| 6100 | M. avium subsp. paratuberculosis | Human | Ileum | ATCC 43015 |
| 187 | M. avium subsp. paratuberculosis | Bovine | Ileum | Recent clinical isolate, NADC |
| 523 | M. avium subsp. paratuberculosis | Bovine | Ileum | |
| 803 | M. avium subsp. paratuberculosis | Bovine | Ileum | |
| 6009 | M. avium subsp. avium | Bovine | | ATCC 35716 (TMC715) |
| 6003 | M. avium subsp. avium | Chicken | | ATCC 35713 (TMC702) |
| 6006 | M. avium subsp. silvaticum | Roe deer | | V1-72 |
| 6076 | M. abscessus | | | ATCC 19977 |
| | M. bovis | Bovine | Lymph node | ATCC 19210 |
| | M. bovis BCG Pasteur | Bovine | Milk | ATCC 35734 |
| 6081 | M. kansasii | Human | | ATCC 12478 |
| 6010 | M. intracellulare | Swine | | ATCC 35773 |
| 6083 | M. phlei | | | ATCC 11758 |
| 6077 | M. scrofulaceum | Human | Lymph node | |

TABLE 2

Oligonucleotide primers used to amplify MAP1643, MAP3840, and MAP0105c

| Primer name | Sequence[a] | Location within gene[b] |
|---|---|---|
| MAP1643F | ATCC<u>TCTAGA</u>ATCGACAAAGAGACGCAAGTCCG | 10 to 32 |
| MAP1643R | GCGC<u>AAGCTT</u>CAACCCTCTTTGGTGATCAGCTT | 2266 to 2287 |
| MAP1643F2 | ATCC<u>TCTAGA</u>CAGTCCATCGACGACCTGTTC | 1021 to 1041 |
| MAP1643R2 | GCGC<u>AAGCTT</u>CACTCGTCGGCGCTCATGTCAGC | 1153 to 1174 |
| MAP3840F | ATCC<u>TCTAGA</u>ATGGCTCGTGCGGTCGGTATCGAC | 1 to 24 |
| MAP3840R | GCGC<u>AAGCTT</u>CACTTGGACTCCCGGTCATCGTC | 1849 to 1872 |
| MAP3840F2 | ATCC<u>TCTAGA</u>GACCGCACCCGTCAGCCGTTCAAG | 859 to 882 |
| MAP3840R2 | GCGC<u>AAGCTT</u>CACGGCTGACGGGTGCGGTCCAG | 856 to 876 |
| 218-4 F | CCTC<u>TCTAGA</u>ATGCGCGGAAACCGCAGCGAG | 163 to 183 |
| 218-4 R | GCGC<u>AAGCTT</u>CATTCGGTGAATGCGCGGAC | 1837 to 1856 |
| 218-9 F | CCTC<u>TCTAGA</u>CGCATGCGATCGAACAGT | 1609 to 1629 |
| 218-9 R | GCGC<u>AAGCTT</u>CAGGTGACGGCGCGTTTGAT | 2587 to 2606 |

[a]Underlined nucleotides represent restriction endonuclease cut sites. The XbaI recognition sequence is TCTAGA, and AAGCTT is the HindIII recognition site.
[b]The numbers represent the nucleotide position within the respective gene. The gene is indicated within the primer name, except that 218-4 F, 218-4 R, 218-9 F, and 218-9 R target MAP0105c.

TABLE 3

Monoclonal antibodies developed in this study

| MAb | Isotype | M. avium subsp. paratuberculosis protein | Protein size (Da) |
|---|---|---|---|
| 11G4 | IgG1, κ[a] | MAP3840 | 66,500 |
| 13A4 | IgG2b, κ | MAP3840 | 66,500 |
| 9G10 | IgG2a, κ | MAP1643 | 85,200 |
| 11F6 | IgG1, κ | MAP1643 | 85,200 |
| 14G11 | IgG1, κ | Unknown | 60,000 |
| 4B6 | IgG1, κ | Unknown | 42,000 |
| 14G3 | IgG2a, κ | Unknown | 28,000 |
| 12C9 | IgG1, κ | Unknown | 21,000 |
| 14D4 | IgG3, κ | Unknown | 35,000 |

[a]κ, kappa chain (light chain of the antibody molecule)

TABLE 4

Oligonucleotide primers used to amplify MAP2121c

| Primer name | Sequence[a] | Location within MAP 2121c[b] |
|---|---|---|
| 2121c-F | ATCC<u>TCTAGA</u>ATGACGTCGGCTCAAAATGAG | 1 to 21 |
| 2121c-R | GCGC<u>AAGCTT</u>CACTTGTACTCATGGAACTG | 904 to 924 |
| 2121c-N-R | GCGC<u>AAGCTT</u>CACTGGATCGTCTGCTCCGGCGT | 442 to 462 |
| 2121c-CenF | ATCC<u>TCTAGA</u>CAGACCTATGTGGACTACGAG | 232 to 252 |
| 2121c-CenR | GCGC<u>AAGCTT</u>CACTTCGTCTTGCCGTCCTCCAC | 676 to 697 |
| 2121c-C-F | ATCC<u>TCTAGA</u>ACGCTGGCCGGGGCTCCCACG | 463 to 483 |

[a]Underlined nucleotides represent restriction endonuclease cut sites. The XbaI recognition sequence is TCTAGA, and AAGCTT is the HindIII recognition site
[b]The numbers represent the nucleotide positions within the gene

I claim:

1. A hybridoma cell line which produces and secretes monoclonal antibodies which selectively bind to *Mycobacterium avium* subspecies *paratuberculosis* produced by the continuous hybridoma cell line having deposit accession number ATCC PTA-122026.

2. A method for detecting *Mycobacterium avium* subspecies *paratuberculosis* in a sample comprising:
   (a) providing a sample of biological material,
   (b) subjecting said sample to an immunosorbent assay using one or more monoclonal antibodies which selectively binds to *Mycobacterium avium* subspecies *paratuberculosis* and which are produced by a hybridoma cell line of claim 1, said monoclonal antibodies forming an immunocomplex with *Mycobacterium avium* subspecies *paratuberculosis* when said *Mycobacterium avium* subspecies *paratuberculosis* is present, and
   (c) detecting said immunocomplex, wherein the detection of said immunocomplex indicates the presence of *Mycobacterium avium* subspecies *paratuberculosis* in said sample.

3. The method of claim 2 wherein said sample is selected from the group consisting of animal tissue and animal fluids.

4. The method of claim 2 wherein said animal is selected from the group consisting of bovine, caprine, and cervidae.

5. The method of claim 4 wherein said animal is a bovine.

* * * * *

SEQUENCE LISTING

<160> NUMBER OF SEQ ID NOS: 18

<210> SEQ ID NO 1
<211> LENGTH: 33
<212> TYPE: DNA
<213> ORGANISM: Mycobacterium avium

<400> SEQUENCE: 1
atcctctaga atcgacaaag agacgcaagt ccg        33

<210> SEQ ID NO 2
<211> LENGTH: 33
<212> TYPE: DNA
<213> ORGANISM: Mycobacterium avium

<400> SEQUENCE: 2
gcgcaagctt caaccctctt tggtgatcag ctt        33

<210> SEQ ID NO 3
<211> LENGTH: 31
<212> TYPE: DNA
<213> ORGANISM: Mycobacterium avium

<400> SEQUENCE: 3
atcctctaga cagtccatcg acgacctgtt c          31

<210> SEQ ID NO 4
<211> LENGTH: 33
<212> TYPE: DNA
<213> ORGANISM: Mycobacterium avium

<400> SEQUENCE: 4
gcgcaagctt cactcgtcgg cgctcatgtc agc        33

<210> SEQ ID NO 5
<211> LENGTH: 34
<212> TYPE: DNA
<213> ORGANISM: Mycobacterium avium

<400> SEQUENCE: 5
atcctctaga atggctcgtg cggtcggtat cgac       34

<210> SEQ ID NO 6
<211> LENGTH: 33
<212> TYPE: DNA
<213> ORGANISM: Mycobacterium avium

<400> SEQUENCE: 6
gcgcaagctt cacttggact cccggtcatc gtc        33

<210> SEQ ID NO 7
<211> LENGTH: 34
<212> TYPE: DNA
<213> ORGANISM: Mycobacterium avium

<400> SEQUENCE: 7
atcctctaga daccgcaccc gtcagccgtt caag       34

<210> SEQ ID NO 8
<211> LENGTH: 33
<212> TYPE: DNA
<213> ORGANISM: Mycobacterium avium

<400> SEQUENCE: 8

-continued

```
gcgcaagctt cacggctgac gggtgcggtc cag                                      33

<210> SEQ ID NO 9
<211> LENGTH: 32
<212> TYPE: DNA
<213> ORGANISM: Mycobacterium avium

<400> SEQUENCE: 9
cctcttctag aatgcgcgga aaccgcagcg ag                                       32

<210> SEQ ID NO 10
<211> LENGTH: 30
<212> TYPE: DNA
<213> ORGANISM: Mycobacterium avium

<400> SEQUENCE: 10
gcgcaagctt cattcggtga atgcgcggac                                          30

<210> SEQ ID NO 11
<211> LENGTH: 29
<212> TYPE: DNA
<213> ORGANISM: Mycobacterium avium

<400> SEQUENCE: 11
cctcttctag acgcatgcga tcgaacagt                                           29

<210> SEQ ID NO 12
<211> LENGTH: 30
<212> TYPE: DNA
<213> ORGANISM: Mycobacterium avium

<400> SEQUENCE: 12
gcgcaagctt caggtgacgg cgcgtttgat                                          30

<210> SEQ ID NO 13
<211> LENGTH: 31
<212> TYPE: DNA
<213> ORGANISM: Mycobacterium avium

<400> SEQUENCE: 13
atcctctaga atgacgtcgg ctcaaaatga g                                        31

<210> SEQ ID NO 14
<211> LENGTH: 30
<212> TYPE: DNA
<213> ORGANISM: Mycobacterium avium

<400> SEQUENCE: 14
gcgcaagctt cacttgtact catggaactg                                          30

<210> SEQ ID NO 15
<211> LENGTH: 33
<212> TYPE: DNA
<213> ORGANISM: Mycobacterium avium

<400> SEQUENCE: 15
gcgcaagctt cactggatcg tctgctccgg cgt                                      33

<210> SEQ ID NO 16
<211> LENGTH: 31
<212> TYPE: DNA
<213> ORGANISM: Mycobacterium avium
```

```
<400> SEQUENCE: 16
atcctctaga cagacctatg tggactacga g                              31

<210> SEQ ID NO 17
<211> LENGTH: 33
<212> TYPE: DNA
<213> ORGANISM: Mycobacterium avium

<400> SEQUENCE: 17
gcgcaagctt cacttcgtct tgccgtcctc cac                            33

<210> SEQ ID NO 18
<211> LENGTH: 31
<212> TYPE: DNA
<213> ORGANISM: Mycobacterium avium

<400> SEQUENCE: 18
atcctctaga acgctggccg gggctcccac g                              31
```